United States Patent
Bahadori

(10) Patent No.: US 12,414,921 B2
(45) Date of Patent: Sep. 16, 2025

(54) METHOD FOR PRODUCING A BIOACTIVE COMPONENT-CONTAINING NANO-COMPOSITE, AND A MONTMORILLONITE-BASED, BIOACTIVE COMPONENT-CONTAINING NANO-COMPOSITE

(71) Applicant: BEZMIALEM VAKIF UNIVERSITESI, Fatih/Istanbul (TR)

(72) Inventor: Fatemeh Bahadori, Fatih/Istanbul (TR)

(73) Assignee: BEZMIALEM VAKIF UNIVERSITESI, Fatih/Istanbul (TR)

( * ) Notice: Subject to any disclaimer, the term of this patent is extended or adjusted under 35 U.S.C. 154(b) by 524 days.

(21) Appl. No.: 17/636,732

(22) PCT Filed: Aug. 20, 2019

(86) PCT No.: PCT/TR2019/050691
§ 371 (c)(1),
(2) Date: Feb. 18, 2022

(87) PCT Pub. No.: WO2021/034281
PCT Pub. Date: Feb. 25, 2021

(65) Prior Publication Data
US 2022/0296525 A1    Sep. 22, 2022

(51) Int. Cl.
*A61K 9/16*   (2006.01)
*A61K 31/12*  (2006.01)
*A61K 31/192* (2006.01)

(52) U.S. Cl.
CPC .......... *A61K 9/1694* (2013.01); *A61K 9/1611* (2013.01); *A61K 31/12* (2013.01); *A61K 31/192* (2013.01)

(58) Field of Classification Search
None
See application file for complete search history.

(56) References Cited

U.S. PATENT DOCUMENTS

| | | | |
|---|---|---|---|
| 2012/0329738 A1* | 12/2012 | Liu | A61K 9/19 514/777 |
| 2015/0257381 A1* | 9/2015 | Ophir | C09D 7/45 424/404 |

FOREIGN PATENT DOCUMENTS

| | | | |
|---|---|---|---|
| KR | 20040020328 A | | 3/2004 |
| KR | 20040020328 | * | 4/2004 |
| TR | 201711955 | * | 9/2017 |
| TR | 201711955 A | | 9/2017 |
| WO | WO 2012164131 | * | 5/2012 |

OTHER PUBLICATIONS

Li et al. "In situ growth of layered double hydroxide on disordered platelets of montmorillonite" 2016.*
Roman et al. "Dexketoprofen and aceclofenac release from layered double hydroxide an SNB-15 ordered mesoporous material" 2016.*
DRUGBANK Dexkeptoprofen.*

* cited by examiner

*Primary Examiner* — Danah Al-Awadi
(74) *Attorney, Agent, or Firm* — Lisa Mueller; Casimir Jones SC

(57) ABSTRACT

The present invention relates to a method for producing a bioactive component-containing nanocomposite, specifically a method for producing a montmorillonite-based, bioactive component-containing nanocomposite, as well as to a montmorillonite-based nanocomposite containing a bioactive component, particularly curcumin or dexketoprofen.

22 Claims, No Drawings

METHOD FOR PRODUCING A BIOACTIVE COMPONENT-CONTAINING NANO-COMPOSITE, AND A MONTMORILLONITE-BASED, BIOACTIVE COMPONENT-CONTAINING NANO-COMPOSITE

TECHNICAL FIELD

The present invention relates to a method for producing a bioactive component-containing nanocomposite, specifically a method for producing a montmorillonite-based, bioactive component-containing nanocomposite, as well as to a montmorillonite-based nanocomposite containing a bioactive component, particularly curcumin or dexketoprofen.

PRIOR ART

Clay has been used by humankind for numerous purposes throughout history. Clay has a multilayer structure, and in general, occurs spontaneously in nature as a result of natural phenomena. Today, clay is used in the fields of food, chemistry, cosmetics, and especially pharmaceuticals, among others, in order to take advantage of said multilayer structure thereof.

In the field of pharmaceuticals, in addition to being used as an active ingredient, there are studies in progress to find a way of employing clay as a drug carrier. The focus of such studies is to place bioactive components between the layers of clay minerals. In general, bioactive components are placed between the layers of clay minerals by means of ion exchange reaction, thus creating a composite structure. In this way, an increase in the availability and mobility of bioactive components in the body, especially of the hydrophobic ones with low water solubility, is achieved by the virtue of the good solubility of such minerals in the water. It is disclosed in the prior art that composite structures with anti-cancer, anti-fungal, anti-hypertensive, anti-inflammatory, analgesic, anti-psychotic, anti-arrhythmic, and anti-oxidant effects are formed by placing various bioactive components between the layers of clay minerals.

Moreover, in the technical field, polymeric chains are also added to the multilayer structure of clay layers to enhance the absorption and the solubility in water, circulation and persistence of the composite structure in the body. Based on the used polymer amount, polymeric chains can be incorporated into a composite structure in one of three different modes, namely in a phase-separated form for micro-composites, or in an intercalated or exfoliated form for nano-composites.

However, said composite applications in the state of the art have many technical problems. One of such problems is that the clay minerals employed in a good number of composite structures are of micron size and therefore the composite structures containing the obtained active substance are also in micron size. Since composite structures of micron size cannot penetrate through the intestinal membrane, the absorption of such structures in the body is low, and accordingly, the efficacy thereof both in topical applications and in the gastrointestinal tract is very low.

Furthermore, as mentioned above, layers may be separated by means of a polymer or macromolecules in order to incorporate bioactive components there between. In this case, for clay minerals of micron size, it is necessary to use a high amount of polymer or macromolecules. In addition, most of the polymers currently being used are synthetic and toxic. In the prior art, this problem has been examined in various studies. The patent application TR 2017/11955 is one example of such studies. In the study, montmorillonite (MMT) clay mineral is reduced to a nano-size to decrease the polymer or macromolecule amount to be used for separating the layers thereof. Although it is possible to reduce MMTs to a nano-size with a variety of methods, mechanical methods such as grinding are used in general, so the yield of such applications is very low. In the abovementioned patent publication, however, a centrifuge method is used in an effort to reduce MMT to a nano-size. Yet the yield of this centrifuge method varies in the range of 20-80% based on the source of clay. Another problem is that organic solvents should be used in this method to be able to load bioactive components between the layers of MMT. In such case, bioactive components are dissolved in an organic solvent in order to load them into MMTs of which layers are separated. During the process of loading, bioactive components enter between the MMT layers together with the organic solvent. Though the aim is to evaporate the organic solvent by spinning the mixture containing the composite structure, the solvent content between the MMT layers cannot be completely evaporated in this method. Even if MMTs of nanoscale are used, a trace amount of said solvents remains within the composite structure in the best scenario. Besides, evaporating organic solvents with a spinning method is both expensive and impractical on the industrial scale. As a result, a drug or food containing a composite structure with a poor toxicity profile is obtained at best.

Curcumin (the bioactive component of turmeric) is a compound with various known benefits which is currently desired to be used as a medicine and/or functional food. However, consuming curcumin with foods other than fatty foods is not an option in daily life as it is not soluble in water. Even if it is consumed, it will be not easy for organs and cells in the body to benefit from curcumin since its absorption in intestines will be very low. This absorption problem is shared by many hydrophobic substances like curcumin, and overcoming this problem is regarded as a need in the technical field. Dexketoprofen is a low water-soluble substance as well, which is used in the treatment of pain and inflammation. The pharmaceutical industry has found trometamol derivative of dexketoprofen to provide water soluble dexketoprofen. However, while trometamol has a very healthy profile, this combination has become an uncomfortable mixture for some people because of the effects of trometamol, such as nausea. Therefore, there is a need for a dexketoprofen-containing, water-soluble drug without any side effects like nausea.

In conclusion, as can be realized from the state of the art, there is a need in the technical field for the development of new formulations in which the toxicity and efficiency of the hydrophobic molecules are improved to increase the mobility and absorption of said molecules in the body.

BRIEF DESCRIPTION OF THE INVENTION

An object of the present invention is to provide a method for producing a nano-composite containing a bioactive component with a low toxicity profile wherein said nano-composite can be formed at a high yield irrespective of the clay source and wherein a high rate of bioactive components can be loaded between the layers of clay mineral without a need of using any organic solvent.

Another object of the present invention is to select the pharmaceutically acceptable clay mineral into which bioactive components can be loaded, from the group consisting of montmorillonite, kaolinite, sepiolite, and combinations thereof. The clay mineral is preferably montmorillonite.

Another object of the present invention is to provide a clay mineral-based, bioactive component-containing nano-composite comprising a high rate of bioactive components between the clay mineral layers which does not contain any organic solvent and thus exhibits a low toxicity profile.

Another object of the present invention is to provide a clay mineral-based, curcumin-containing nano-composite comprising a high rate of bioactive components between the clay mineral layers which does not contain any organic solvent and thus exhibits a low toxicity profile.

Another object of the present invention is to provide a clay mineral-based, dexketoprofen-containing nano-composite comprising a high rate of bioactive components between the clay mineral layers which does not contain any organic solvent and thus exhibits a low toxicity profile.

DETAILED DESCRIPTION OF THE INVENTION

In one embodiment of the present invention, a nano-composite production method comprising the following steps is disclosed:
a) homogenizing a pharmaceutically acceptable layered clay mineral with a solvent;
b) spray drying the homogenate obtained in step a) to form a nano-clay mineral;
c) homogenizing the nano-clay mineral obtained in step b) with a solvent;
d) homogenizing the homogenate of nano-clay mineral obtained in step c) with at least one nontoxic macromolecule to incorporate said macromolecule between the layers of nano-clay mineral; and
e) homogenizing the nanocomposite obtained in step d) with at least one bioactive component to ensure that said bioactive component adheres to the macromolecule.

The term "layered clay mineral" as used herein means a clay mineral in a structure with several juxtaposed layers. The pharmaceutically acceptable clay mineral according to the present invention is selected from the group consisting of montmorillonite, kaolinite, sepiolite, and mixtures thereof, and is preferably montmorillonite. In a method for producing a bioactive component-containing nano-composite according to the present invention, the ratio of a clay mineral to a solvent in the step a) is preferably in the range of 1:10 to 1:100 (weight/volume), and more preferably in the range of 1:40 to 1:80 (weight/volume). The unit "weight/volume" as used herein represents the ratio of a clay mineral in a particular weight to a solvent in a particular volume. According to the present invention, the most preferred weight/volume ratio is 1:50.

The solvent used in the method according to the present invention may be a polar, protic or aprotic solvent. The solvent is not organic and the solvent is preferably water or water-based solvent and more preferably water.

In the present invention, the first and second homogenization step a) and c) are accomplished through a homogenizer operating at from 2,000 to 10,000 RPM. more preferably at from 2.200 to 4,000 RPM, and particularly preferably at from 2.500 to 3.500 RPM. The homogenization of clay mineral may not be achieved due to the tendency of clay minerals to agglomerate at a speed below the above-mentioned range of homogenizer revolution speed, whereas the layered structure of clay mineral breaks down at a speed above the same.

The homogenizer used in the present invention is preferably Silverson® Homogenizer Mixer Model Ex60 with Heavy Duty Adjustable. According to the present invention, the homogenization step a) and c) comprises adding the solvent to the homogenizator after the clay mineral. Thus, solvents are preferably added on the clay mineral. Thereby, formation of insoluble aggregates caused by adding firstly the clay mineral after solvent is prevented. The production method according to the present invention further comprises a step of incubating the solvent-homogenized clay mineral from the step a) for a predetermined period of time before spray drying. Following incubation, a precipitate is deposited at the bottom of the mixture. The precipitate formed during incubation period are separated from the mixture of solvent-clay mineral. Thus, a more homogenous and pure composite can be obtained, which can be named as supernatant. Incubation is preferably carried out under room conditions (21-25° C. and 35-55% relative humidity). Incubating under a higher temperature may lead to a decrease in the rate of solvent in the mixture of clay mineral-solvent, resulting in calcification of the mixture. Also, if the mixture is kept under a higher humidity, a high rate of swelling may occur in the clay. Here, the predetermined period of time is preferably in the range of 4 to 20 hours, and more preferably in the range of 6 to 10 hours. Implementing a period of time shorter than the preferred predetermined period of time may lead to an incomplete precipitation of impurities that might be present in the clay mineral, resulting in transport of such impurities into the solvent. Thus, such substances may be removed with the solvent, which causes inefficiency. On the other hand, at a period of time longer than the preferred predetermined period of time, an over-swelling of clay mineral leading to gelling occurs in the solvent which may ultimately cause a loss of the proper form for creating a composite structure.

In the production method according to the present invention, the clay mineral (supernatant) obtained in step b) is spray dried to obtain a nano-clay mineral.

The diameter of spray nozzle of the spray dryer used in the process according to the present invention is preferably in the range of 20 to 140 micrometers, and the evaporation capacity of the same spray dryer is preferably in the range of 40 to 220 kg/hours. The ambient temperature during drying with spray dryer in the present invention is in the range of from 110° C. to 150° C. In addition, the preferred spray nozzle diameter is 70 microns, the preferred evaporation capacity is 100 kg/hours, and the preferred ambient temperature is 130° C. The spray dryer used in the present invention is preferably Bakon® Industrial Spray Dryer.

According to the present invention, dilution of the feeding mixture before spray drying can be needed in order to protect the nozzle from clogging. However, this dilution step does not have any effect on the size or quality of the produced product.

The clay mineral swollen upon homogenization is suspended in solvent depending upon its size after incubation for a predetermined period of time. While nano-sized tiny particles may be present in the upper parts of the mixture, the number of larger, inefficient particles increases towards the lower parts of the same. The sizes of clay mineral particles suspended in the different parts may be equal to the upper or lower limits of the respective ranges depending upon the clay source. When a poor source of clay is employed, the nano-clay mineral particles in the upper parts will have to be used because of that fact that micron-sized clay mineral particles will be present even in the middle parts of the solvent-clay mineral mixture in such a case. Other clay mineral particles in the other parts of the solvent-clay mineral mixture will not be used efficiently due to their sizes. On the other hand, in a good clay source, mineral particles in the lowermost part of the solvent-clay mineral mixture will not be used efficiently due to their sizes. In the method for producing a bioactive component-containing nano-composite according to the present invention, however, clay mineral particles are reduced in size by subjecting the solvent-clay mineral mixture to the spray dryer to break said particles. Thus, the clay mineral particles suspended in the middle or even lower parts of the solvent-clay mineral mixture can be reduced to sizes below 300 nm in order to be used for forming a composite structure.

As a non-limiting example, when montmorillonite particles with an average diameter of 100 microns are subjected to a spray dryer with a spray nozzle diameter of 70 microns, the size of montmorillonite particles can be reduced to 300 nm at a rate of 80%. As a result, montmorillonite particles are obtained at a high yield irrespective of the clay source. Thus, dependence on a particular clay source is eliminated. Also, the cost of reducing montmorillonites to a nano-size is significantly decreased compared to other inefficient methods such as grinding. The distribution of montmorillonites in the body, and the rate of macromolecules to be placed between the montmorillonite layers are significantly increased.

Clay mineral particles of 4-20 nm, 20-500 nm, and 500 nm-10,000 microns are suspended in the upper, middle, and lower parts of the solvent-clay mineral mixture, respectively. The upper part as mentioned herein varies depending upon the quality of the clay. The upper part and the clay minerals according to the present invention constitute at least 20% of the mixture, and preferably vary in the range of from 20% to 50%.

In the next stage of the production method according to the present invention, nano-clay mineral is homogenized again after spray drying (step c) of the production method). As being at the first homogenization step (step a) of the production method), nano-clay mineral is mixed and homogenized with a solvent (particularly water, or a water-based solvent) by means of a homogenizer preferably at a ratio in the range of 1:10 to 1:100 (weight/volume), or particularly preferably at a ratio in the range of 1:40 to 1:80 (weight/volume) (e.g. 1 g of nano-clay mineral/50 ml of solvent). The preferred weight/volume ratio is 1:50. The revolution speed of homogenizer is preferably in the range of 2,000-10,000 RPM, particularly preferably in the range of 2,000 to 4,000 RPM, and most preferably 3,000 RPM. The homogenization of nano-clay mineral may not be achieved due to the trendy of the same to agglomerate at a speed below the abovementioned range of homogenizer revolution speed, whereas the layered structure of nano-clay mineral breaks down at a speed above the same.

In the preferred weight/volume ratio of the present invention, the nano-composite obtained from a clay mineral homogenized with a solvent is able to serve as an efficient drug carrier, and also, the possibility of sludging which might occur in case of an excess solvent is avoided.

In the following step d), the homogenate of nano-clay mineral obtained in step c) is homogenized with nontoxic macromolecules via the homogenizer. Thus, such macromolecules are placed between the layers of nano-clay mineral. These macromolecules include, without limitation, emulgators, polymeric materials, phospholipids, surfactants, glycolipids, tannins, polysaccharides, and fatty acids. Here, the ratio of macromolecule to the nano-clay mineral mixture is preferably in the range of 0.01% to 0.1%. The revolution speed of homogenizer during the homogenization of nano-clay mineral together with macromolecules is preferably in the range of 3,000 to 22,000 RPM, more preferably in the range of 8,000 to 20,000 RPM, and most preferably in the range of 9,000 to 11,000 RPM. A homogenization at a speed within said range allows maintaining a high level of adhesion rate for macromolecules between the layers of nano-clay mineral, and ensures the integrity and stability of the layers of nano-clay mineral. When the homogenization is carried out at a speed within said range, the clay layers diverge, the macromolecules enter between them, and the clay layers reunite without breaking down. The preferred macromolecule is an emulgator, and the preferred ratio of macromolecule to the nano-clay mineral mixture is 0.01%. In the present invention, the emulgator is selected from the group comprised of triethyl citrate, glyceryl diacetate, glyceryl triacetate, propylene glycol, and combinations thereof.

In the method according to the present invention, the nano-clay mineral mixture having macromolecules placed between the layers of clay mineral as obtained from the step d) (the homogenate of nano-clay mineral) is homogenized again with a bioactive component by means of a homogenizer. In this way, bioactive components are drawn towards the nano-clay mineral layers, bioactive components interact with macromolecules, and thus, bioactive components are adhered to macromolecules. Owing to this homogenization step, the need for dissolving bioactive components in an organic solvent is eliminated. As a result, a bioactive component-containing nano-composite is obtained.

Each homogenization step in the method of the present invention is preferably carried out for a period of 10-30 minutes.

In an embodiment of the present invention, said bioactive component may be a hydrophobic active substance, and is preferably curcumin or one of its derivatives, i.e. curcuminoids (generally obtained from "*Curcuma longa*" rhizomes). The ratio of the bioactive component curcuminoid to the nano-clay mineral is preferably 5% by weight, and the revolution speed of homogenizer is preferably between 15,000 to 25,000 and most preferably 20,000 RPM.

In a curcumin-containing nano-composite prepared by the method of the present invention, the water solubility and intestinal permeability of curcumin are 80,000 and 50 times higher, respectively.

In the step of ensuring adhesion of bioactive components to macromolecules in the method according to the present invention, the proportion of bioactive components in the nano-clay mineral mixture is in the range of from 1% to 50% by weight, and the revolution speed of homogenizer is preferably in the range of 3,000 to 20,000 RPM.

In another embodiment of the present invention, the bioactive component is preferably dexketoprofen. The ratio of the bioactive component dexketoprofen to the nano-montmorillonite is preferably 5% by weight, and the revolution speed of homogenizer is preferably between 15,000 to 25,000 and most preferably 20,000 RPM.

By said steps, macromolecules are placed between the layers of nano-clay mineral. In other words, it is ensured that macromolecules adhere between the layers of clay mineral. When the macromolecules having a long chain structure enter between the layers of nano-clay mineral, they will also interact with the bioactive components, which are smaller molecules, as a result of the subsequent steps. In other words, the bioactive components will adhere to the macromolecules. Thereby, the macromolecules placed between the layers of nano-clay mineral will serve as a carrier for the bioactive components.

The bioactive component-containing nano-composite obtained by the method of the present invention is in a liquid form.

If a solid form of a bioactive component-containing nano-composite is desired, the present invention may also include the step of solidification step of nano-composite obtained in step e) by spray drying; which means as converting the liquid-phase bioactive component-containing nano-composite obtained in step e) to a solid form by means of a spray dryer. Therefore, the spray dryer used in the step of obtaining a bioactive component-containing nano-clay mineral may also be used for obtaining a solid form of the same bioactive component-containing nano-clay mineral. Thus, both liquid and solid forms of a bioactive component-containing nano-composite can be obtained in a single production line and the production costs are reduced.

A bioactive component-containing nano-composite in a solid phase according to the present invention can be useful in production of oil-based or water-based creams, pomades and ointments.

For example, an effective oil-based or water-based cream, pomade or ointment for the treatment of eczema can be obtained by introducing a curcumin-containing nano-composite to the production of the same. Moreover, a bioactive component capsule with an improved bioavailability can be obtained by filling capsules with such solid-phase bioactive component-containing nano-composite. For instance, curcumin capsules can be obtained by filling a powdered curcumin-containing nano-composite into capsules. In another exemplary embodiment, curcumin tea bags can be obtained by adding a powdered curcumin-containing nano-composite to a dry tea mixture.

In an exemplary embodiment of the present invention, a nano-composite is provided wherein a number of nontoxic emulgator molecules (e.g. glyceryl monostearate) are located between the layers of nano-sized montmorillonite, and such emulgators adhere both between the layers and to a number of curcuminoid molecules. In an exemplary production method according to this embodiment of the present invention, 100 g of montmorillonite is homogenized at 3,000 RPM with 1 L (1:10 weight/volume ratio) of water serving as a solvent. Following a predetermined incubation period of 6 hours, the residues deposited at the bottom are separated from the mixture of water-montmorillonite. The homogenized water-montmorillonite mixture is dried by means of a spray dryer at 130° C. and at a rate of 70 kg/hours to obtain a number of nano-montmorillonite particles which are smaller than 300 nm. The nano-montmorillonite is homogenized again at 3,000 RPM with a 1:10 weight/volume of water serving as a solvent. Preferably, 100 mg of glyceryl monostearate dissolved in 50 ml of water is added to the homogenized water-nano-montmorillonite mixture, and then, homogenization is continued at 15,000 RPM. Thereafter, 5 g of powdered curcumin is added to the mixture, and homogenization is continued until the mixture becomes a homogenous orange color. As a result, a liquid-phase curcumin-containing nano-composite is obtained.

In another exemplary embodiment of the present invention, a nano-composite is provided wherein a number of nontoxic emulgator molecules (e.g. glyceryl monostearate) are located between the layers of nano-sized montmorillonite, and such emulgators adhere both between the layers and to a number of dexketoprofen molecules. In an exemplary production method according to the this embodiment of the present invention, 100 g of montmorillonite is homogenized at 3,000 RPM with 1 L (1:10 weight/volume ratio) of water serving as a solvent. Following a predetermined incubation period of 6 hours, the residues deposited at the bottom are separated from the mixture of water-montmorillonite. The homogenized water-montmorillonite mixture is dried by means of a spray dryer at 130° C. and at a rate of 70 kg/hours to obtain a number of nano-montmorillonite particles which are smaller than 300 nm. The nano-montmorillonite is homogenized again at 3,000 RPM with a 1:10 weight/volume of water serving as a solvent. Preferably, 100 mg of glyceryl monostearate dissolved in 50 ml of water is added to the homogenized water-nano-montmorillonite mixture, and then, homogenization is continued at 15,000 RPM. Thereafter, 2.5 g of dexketoprofen is added to the mixture, and homogenization is continued until the mixture becomes a homogenous orange color. As a result, a liquid-phase dexketoprofen-containing nano-composite is obtained.

The method for producing a bioactive component-containing nano-composite according to the present application provide a reduction for the cost of producing a bioactive component-containing nano-composite. In addition, due to the use of carrier macromolecules in the present method, it is now possible to place a higher rate of bioactive components between the nano-clay mineral layers compared to the prior art. Thus, consumers can benefit more from bioactive components, especially from those insoluble in water. Besides, since no organic solvent is used, a bioactive component-containing nano-composite with a low toxicity profile can now be obtained.

The obtained bioactive component-containing nano-composite is in a liquid phase. This liquid-phase bioactive component-containing nano-composite may be mixed with a drink (e.g. fruit juice, cold tea, ayran, or water) to obtain a bio-drink (e.g. curcumin/dexketoprofen drink) in which the bioavailability of the bioactive component is improved and the taste of the same is suppressed.

The present invention provides a nano-composite wherein a number of nontoxic emulgator molecules are located between the layers of nano-sized montmorillonite, and such emulgators adhere both between the layers and to a number of curcuminoid molecules. The bitter taste of curcuminoids is concealed as curcuminoid molecules are wrapped up by the montmorillonite layers. Thus, by incorporating curcuminoid molecules into said nano-composite drinks, it can be ensured that consumers benefit from such molecules.

Unless otherwise defined, all technical and scientific terms used herein have the same meaning as commonly understood by one of ordinary skill in the art. In addition, the materials, methods, and examples are illustrative only and not intended to be limiting.

The invention now will be described in particularity with the following illustrative examples; however, the scope of the present invention is not intended to be, and shall not be, limited to the exemplified embodiments below.

EXAMPLES

Example 1

Production Method of Curcumin-Containing Nano-Montmorillonite Composite
  a) homogenizing 100 g of montmorillonite with 1 L of water (1:10 weight/volume ratio) by means of a high-shear homogenizer at 3,000 RPM,
  b) incubating the homogenate obtained in step a) for 6 hours under room conditions,
  c) separating the precipitate deposited at the bottom of the mixture and obtaining a supernatant, d) spray drying the supernatant at spray dryer equipped with a pressure nozzle of 70 μm with a water evaporating capacity of 100 kg/h at 130° C. in order to obtain a nano-montmorillonite, e) homogenizing nano-montmorillonite obtained in step d) with water by means of a high-shear homogenizer at 3,000 RPM wherein the weight ratio of montmorillonite to water is 1:10 (weight/volume), f) dissolving 100 mg of glyceryl monostearate in 50 ml of water in order to obtain a glyceryl monostearate mixture, g) homogenizing the homogenate obtained in step e) with the glyceryl monostearate mixture by means of high-shear homogenizer at 15,000 RPM h) homogenizing the homogenate obtained in step g) with 5 g of powdered curcumin by means of high-shear homogenizer at 15,000 RPM i) obtaining a liquid of curcumin-containing nano-montmorillonite composite j) spray drying the liquid obtained in step i) at spray dryer equipped with a pressure nozzle of 20 μm with a water evaporating capacity of 100 kg/h at 130° C. in order to obtain a solid curcumin-containing nano-montmorillonite composite

The invention claimed is:

1. A method for producing a bioactive component-containing nano-composite, comprising the following steps:
   a) homogenizing a pharmaceutically acceptable layered clay mineral with a solvent, wherein homogenization is accomplished using a homogenizer operating at from 2,000 to 10,000 RPM;
   b) spray drying the homogenate obtained in step a) to form a nano-clay mineral;
   c) homogenizing the nano-clay mineral obtained in step b) with a solvent, wherein homogenization is accomplished using a homogenizer operating at from 2,000 to 10,000 RPM;
   d) homogenizing the homogenate of nano-clay mineral obtained in step c) with at least one nontoxic macromolecule to incorporate said macromolecule between the layers of nano-clay mineral, wherein homogenization is accomplished using a homogenizer operating at from 8,000 to 20,000 RPM; and
   e) homogenizing the nanocomposite obtained in step d) with at least one bioactive component to ensure that said bioactive component adheres to the macromolecule, wherein the proportion of bioactive components in the nano-clay mineral mixture is in the range of from 1% to 50% by weight and the revolution speed of the homogenizers is in the range of 3,000 to 20,000 RPM.

2. The method according to claim 1, wherein the ratio of the clay mineral to the solvent in the step a) or the ratio of the nano-clay mineral to the solvent in the step c) is in the range of 1:10 to 1:100 weight/volume.

3. The method according to claim 2, wherein the ratio of the clay mineral to the solvent in the step a) or the ratio of the nano-clay mineral to the solvent in the step c) is in the range of 1:40 to 1:80 weight/volume.

4. The method according to claim 1, wherein the solvent in steps a) and c) is not organic.

5. The method according to claim 4, wherein the solvent is water.

6. The method according to claim 1, wherein the homogenization step a) and c) are accomplished through a homogenizer operating at from 2,200 to 4,000.

7. The method of claim 1, wherein the homogenization step a) and c) comprises adding the solvent to the homogenizator after the clay mineral.

8. The method according to claim 1, further comprising the step of incubating the solvent-homogenized clay mineral obtained in step a) for a predetermined period of time before spray drying and separating the precipitate formed during the incubation period.

9. The method according to claim 8, wherein the predetermined period of time is from 4 to 20 hours.

10. The method according to claim 8, wherein the incubation is carried out under room conditions which is at a temperature of 21-25° C. and 35-55% relative humidity.

11. The method according to claim 1, wherein the spray drying in step b) comprises using a spray dryer and the spray dryer has a spray nozzle diameter in the range of 20 to 140 micrometers.

12. The method according to claim 1, wherein the spray drying in step b) is carried out at a temperature of 100 to 150° C.

13. The method according to claim 1, wherein the homogenization step d) is accomplished through a homogenizer operating at from 9,000 to 11,000 RPM.

14. The method according to claim 1, wherein the macromolecule in the step d) is in the range of 0.01 to 0.1% by weight of the homogenized nano-clay mineral.

15. The method according to claim 1, wherein the macromolecule in the step d) is selected from the group consisting of emulgators, polymeric materials, phospholipids, surfactants, glycolipids, tannins, polysaccharides fatty acids and combinations thereof.

16. The method according to claim 15, wherein the macromolecule is an emulgator.

17. The method according to claim 16, wherein the emulgator is selected from the group consisting of triethyl citrate, glyceryl diacetate, glyceryl triacetate, propylene glycol and combinations thereof.

18. The method according to claim 1, wherein the clay mineral is selected from the group consisting of montmorillonite, kaolinite, sepiolite and combinations thereof.

19. The method according to claim 18, wherein the clay mineral is montmorillonite.

20. The method according to claim 1, wherein the bioactive substance is a curcuminoid.

21. The method according to claim 1, wherein the bioactive substance is dexketoprofen.

22. The method according to claim 1, further comprising a solidification step of nano-composite obtained in step e) by spray drying.

* * * * *